United States Patent
Hara

(10) Patent No.: US 11,036,961 B2
(45) Date of Patent: Jun. 15, 2021

(54) STRIPED PATTERN IMAGE EXAMINATION SUPPORT APPARATUS, STRIPED PATTERN IMAGE EXAMINATION SUPPORT METHOD, AND PROGRAM

(71) Applicant: NEC Corporation, Tokyo (JP)

(72) Inventor: Masanori Hara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 84 days.

(21) Appl. No.: 16/344,123

(22) PCT Filed: Oct. 25, 2017

(86) PCT No.: PCT/JP2017/038594
§ 371 (c)(1),
(2) Date: Apr. 23, 2019

(87) PCT Pub. No.: WO2018/079630
PCT Pub. Date: May 3, 2018

(65) Prior Publication Data
US 2020/0065546 A1    Feb. 27, 2020

(30) Foreign Application Priority Data
Oct. 26, 2016  (JP) .............................. JP2016-209502

(51) Int. Cl.
*G06K 9/00*   (2006.01)
*G06K 9/46*   (2006.01)

(52) U.S. Cl.
CPC ........... *G06K 9/0008* (2013.01); *G06K 9/001* (2013.01); *G06K 9/00093* (2013.01); *G06K 9/46* (2013.01)

(58) Field of Classification Search
None
See application file for complete search history.

(56) References Cited

U.S. PATENT DOCUMENTS 6,134,340 A * 10/2000 Hsu ..................... G06K 9/00087
382/124
7,295,688 B2  11/2007 Hara et al.
(Continued)

FOREIGN PATENT DOCUMENTS

| JP | 2004078433 A | 3/2004 |
| JP | 2004078434 A | 3/2004 |
| WO | 2013145383 A1 | 10/2013 |

OTHER PUBLICATIONS

"*Information Technology*: American National Standard for Information Systems—Data Format for the Interchange of Fingerprint, Facial, & Scar Mark & Tattoo (SMT) Information", NIST Special Publication 500-245, Sep. 2000, ANSI/NIST-ITL Jan. 2000, Revision of ANSI/NIST-CSL Jan. 1993 & ANSI/NIST-ITL 1a-1997 (81 Pages Total).

(Continued)

*Primary Examiner* — Leon Viet Q Nguyen
(74) *Attorney, Agent, or Firm* — Sughrue Mion, PLLC

(57) ABSTRACT

A striped pattern image examination support apparatus includes a feature extraction part, a central line collation part, and a display part. The feature extraction part extracts, from each of a first striped pattern image and a second striped pattern image, at least central lines and feature points, as a feature of each of the first striped pattern image and the second striped pattern image. The central line collation part performs collation of the respective central lines of the first striped pattern image and the second striped pattern image, and computes corresponding central lines between the first striped pattern image and the second striped pattern image. The display part determines a display form of each of the central lines based on the computed corresponding central lines and superimposes and displays the central lines on each of the first striped pattern image and (Continued)

the second striped pattern image, according to the determined display form.

9 Claims, 13 Drawing Sheets

(56) References Cited

U.S. PATENT DOCUMENTS

| | | |
|---|---|---|
| 7,333,641 B2 | 2/2008 | Hara et al. |
| 2003/0161502 A1* | 8/2003 | Morihara ............ G06K 9/00026 382/115 |
| 2004/0032976 A1 | 2/2004 | Hara et al. |
| 2004/0101173 A1 | 5/2004 | Hara et al. |
| 2013/0216106 A1 | 8/2013 | Hara et al. |
| 2015/0088863 A1 | 3/2015 | Horiba et al. |
| 2015/0220769 A1 | 8/2015 | Hara et al. |
| 2016/0196461 A1 | 7/2016 | Hara |

OTHER PUBLICATIONS

D. Maltoni et al., Handbook of Fingerprint Recognition, Fingerprint Analysis and Representation, 1997, pp. 83-113 (31 pages total).
USDOJ; FBI; John Edgar Hoover, The Project Gutenberg EBook of the Science of Fingerprints, The Science of Fingerprints, Classification and Uses, Aug. 10, 2006 (128 Pages total).
"The Fingerprint Sourcebook", U.S. Department of Justice Office of Justice Programs National Institute of Justice, 2004 (422 pages total).
Extended European Search Report for EP Application No. EP17865753.2 dated Sep. 18, 2019.

* cited by examiner (b)

(a)

(b)

(a)

(b)

(a)

STRIPED PATTERN IMAGE EXAMINATION SUPPORT APPARATUS, STRIPED PATTERN IMAGE EXAMINATION SUPPORT METHOD, AND PROGRAM

TECHNICAL FIELD

Cross-Reference to Related Applications

This application is a National Stage Entry of PCT/JP2017/038594 filed on Oct. 25, 2017, which claims priority from Japanese Patent Application 2016-209502 filed on Oct. 26, 2016, the contents of all of which are incorporated herein by reference, in their entirety.

The present invention relates to a striped pattern image examination support apparatus, a striped pattern image examination support method, and a program. More specifically, the invention relates to a striped pattern image examination support apparatus, a striped pattern image examination support method, and a program for supporting examination of two images such as fingerprints or palmprints (determination whether the striped pattern images are identical or not).

BACKGROUND ART

A fingerprint composed of a lot of ridges in a striped pattern is said to have two remarkable features that the fingerprint is invariant throughout life and is not the same for anyone. Thus, the fingerprint has been used as means for personal identification for a long time.

In a fingerprint examination or a difference determination of fingerprints as to whether or not two fingerprints belong to a same finger, an examiner (examiner) looks and compares two fingerprint images and visually determines whether or not feature points are present at corresponding positions on ridges of the two fingerprints. If the number of the feature points that become pairs between the two fingerprints or the feature points that are present at the corresponding positions on the ridges of the two fingerprints is a certain number or more, it is determined that the two fingerprints belong to the same finger. The ridges are linear elevations that are present on the skin of a finger or a palm, or a striped pattern in a fingerprint or a palmprint that has been applied by the linear elevations.

In a fingerprint image or a palmprint image, a feature point often indicates an ending point or a bifurcation point of a ridge that constitutes a stripe. Feature points that become a pair in two images (fingerprint images in this case) are referred to as paired feature points.

A material indicating a relation between paired feature points that have been confirmed is presented in a trial or the like, together with two fingerprint photographs and fingerprint grayscale images that have been disposed side by side. Non Patent Literature 1 describes an example of the material that is presented in the trial, for example.

In recent years, a fingerprint collation system using a computing machine (such as an information processing apparatus or a computer) has been spreading. Therefore, an evidentiary material for a trial is often prepared by using the computer. Usually, a work of displaying two fingerprint images side by side, connecting paired feature points on the two fingerprint images by a line, and describing a number given to the paired feature points is referred to as charting. A function of displaying two fingerprints and supporting manual input or modification of the paired feature points in a system for preparing the material for the trial using the computer is referred to as a charting function (Charting Function).

The computing machine including the charting function often displays two fingerprints for a difference determination from side from side. Such a display method is referred to as a side by side (side by side) display. Diagrams or screens for which the side by side display has been performed is also referred to as a charting diagram or a feature point chart diagram. On a charting screen, a line connecting two corresponding feature points is also often displayed.

When confirming corresponding feature points, usually, an examiner visually confirms whether ridges that are present in the vicinity of the feature points of interest on two fingerprint images for examination are identical or not. When two fingerprints for the examination including the vicinity ridges match, the examiner determines that the confirmed corresponding feature points are correct. However, it is not easy to determine whether the ridges that are present in the vicinity of the feature points of interest are identical or not.

In a trial having a jury system such as the one in the United States, explanation of fingerprint identicalness to a jury (non-expert of a fingerprint) is required. It is not, however, easy to explain to such a non-expert about determination whether ridges are identical or not. Then, Non Patent Literature 2 proposes a method of coloring corresponding ridges in order to facilitate determination whether ridges in the vicinity of feature points are identical or not.

[NPL 1] Page 193-196 of "The science of Fingerprints Classification and Uses" (by John Edgar Hoover, US DOJ, FBI; Rev. 12-84, 1990)

[NPL 2] VanDam Page—Updated 3-28-06, "a place for Friction Ridge Examiners to access information about the discipline of Friction Ridge and Latent Print Examination", [online], [searched on Oct. 12, 2016], Internet <URL: http://www.clpex.com/VanDam.htm>

SUMMARY

Each disclosure of the above-listed Citation List is incorporated herein in its entirety by reference. The following analysis has been made by the inventors of the present invention.

The surface of a finger or a palm is soft and easy to be deformed. Thus, it is usual that even if a same finger or a same palm is used, the shape of a fingerprint or a palmprint taken as an image is different for each image. Consequently, even if two fingerprint images or two palmprint images for examination are generated from an identical fingerprint or an identical palmprint, ridges are not overlapped with each other even by translation or rotation.

Further, when a region with an unclear ridge is included due to bad quality of a fingerprint image, for instance, in such a case as when one of fingerprint images for examination is a remaining fingerprint, it is difficult to determine whether individual ridges in the vicinity of feature points are identical or not, so that an erroneous determination may be performed for fingerprints as a whole.

In the method of distinguishing the corresponding ridges by using a color described in Non Patent Literature 2, determination whether the individual ridges in the vicinity of the feature points are identical or not can be clearly made. Determination whether whole fingerprints are identical or not can be thereby facilitated. However, this method is carried out by manually performing coloring of the individual ridges using a commercial graphic tool, so that a lot of man-hours are required.

It is an object of the present invention to provide a striped pattern image examination support apparatus, a striped pattern image examination support method, and a program for supporting striped pattern image examination of determining whether or not two striped pattern images are generated from a same object.

According to a first aspect of the present invention or disclosure, there is provided a striped pattern image examination support apparatus comprising:

a feature extraction part to extract at least central lines and feature points from each of first and second striped pattern images, as a feature of each of the first and second striped pattern images;

a central line collation part to perform collation of the respective central lines of the first striped pattern image and the second striped pattern image and compute corresponding central lines between the first and second striped pattern images; and a display part to determine a display form of each of the central lines based on the computed corresponding central lines and superimpose and display the central lines on each of the first and second striped pattern images, according to the determined display form.

According to a second aspect of the present invention or disclosure, there is provided a striped pattern image examination support method comprising:

extracting at least central lines and feature points from each of first and second striped pattern images, as a feature of each of the first and second striped pattern images;

performing collation of the respective central lines of the first striped pattern image and the second striped pattern image and computing corresponding central lines between the first and second striped pattern images; and determining a display form of each of the central lines based on the computed corresponding central lines and superimposing and displaying the central lines on each of the first and second striped pattern images, according to the determined display form.

According to a third aspect of the present invention or disclosure, there is provided a program configured to cause a computer to execute:

a process of extracting at least central lines and feature points from each of first and second striped pattern images, as a feature of each of the first and second striped pattern images;

a process of performing collation of the respective central lines of the first striped pattern image and the second striped pattern image and computing corresponding central lines between the first and second striped pattern images; and a process of determining a display form of each of the central lines based on the computed corresponding central lines and superimposing and displaying the central lines on each of the first and second striped pattern images, according to the determined display form.

This program can be recorded on a computer-readable storage medium. The storage medium can be set to a non-transient (non-transient) one such as a semiconductor memory, a hard disk, a magnetic recording medium, or an optical recording medium. The present invention can also be embodied as a computer program product.

According to each aspect of the present invention, there are provided a striped pattern image examination support apparatus, a striped pattern image examination support method, and a program for supporting striped pattern image examination to determine whether or not two striped pattern images are the ones generated from a same object.

BRIEF DESCRIPTION OF DRAWINGS

FIG. 7 includes FIG. 7A and FIG. 7B in which FIG. 7A is a diagram where extracted central lines are superimposed on the remaining fingerprint illustrated in FIG. 5, and FIG. 7B is a diagram where extracted feature points and so on are superimposed on the remaining fingerprint illustrated in FIG. 5.

FIG. 8 includes FIG. 8A and FIG. 8B in which FIG. 8A is a diagram where extracted central lines are superimposed on a fingerprint image illustrated in FIG. 6, and FIG. 8B is a diagram where extracted feature points and so on are superimposed on the fingerprint image illustrated in FIG. 6.

FIG. 11 includes FIG. 11A and FIG. 11B in which FIG. 11A is a diagram illustrating an example where, with respect to five feature points illustrated in FIG. 9 and having the different feature point types, the feature point types in the remaining fingerprint have been manually modified by a user, and FIG. 11B is a diagram for explaining generation of each central line that matches a manual feature point.

PREFERRED MODES

Figure 1:
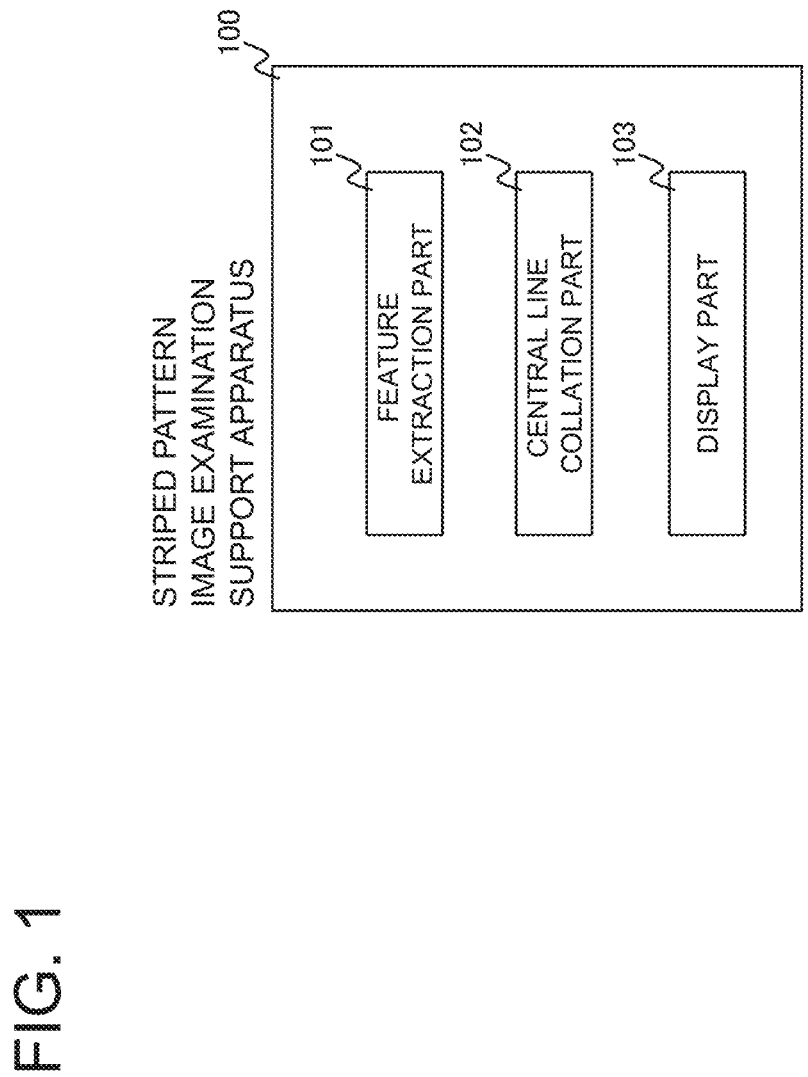
FIG. 1 is a diagram for explaining an overview of an exemplary embodiment.

First, an overview of an exemplary embodiment of the present invention will be described. A reference numeral in each drawing given in this overview is given to each element for convenience as an example for helping understanding, and the description of this overview does not intend to impose any limitation.

A striped pattern image examination support apparatus 100 according to the exemplary embodiment includes a feature extraction part 101, a central line collation part 102, and a display part 103. The feature extraction part 101 extracts at least central lines and feature points from each of a first striped pattern image and a second striped pattern image as a feature of each of the first striped pattern image and the second striped pattern image. The central line collation part 102 performs collation of the respective central lines of the first striped pattern image and the second striped pattern image, thereby computing corresponding central lines between the first and second striped pattern images. The display part 103 determines the display form of each of the central lines based on the computed corresponding central lines and superimposes and displays the central lines on each of the first and second striped pattern images, according to the determined display form.

The striped pattern image examination support apparatus 100 computes the central lines (corresponding central lines; ridge charts) that constitute a pair between two striped pattern images. Then, based on the computed corresponding central lines, the striped pattern image examination support apparatus 100 selects the display form of each of the lines to be displayed on each of the two striped pattern images. To take an example, the striped pattern image examination support apparatus 100 distinguishes the corresponding central lines and a noncorresponding central line (central line of one of the two images for which a central line that becomes a pair between the two images does not present on the other image) by using different colors, thereby allowing distinction between the corresponding central lines and the noncorresponding central line by a user (such as an examiner). Alternatively, the striped pattern image examination support apparatus 100 highlights the noncorresponding central line among the central lines included in each of the two striped pattern images, thereby allowing recognition of the presence of the noncorresponding central line by the user.

By checking the display that is presented by the striped pattern image examination support apparatus 100, the user can readily determine whether or not the two fingerprint images indicate fingerprints of a same finger. That is, if there is no noncorresponding central line, the user can readily determine that the two images are images of the same finger. As mentioned above, the striped pattern image examination support apparatus 100 is an apparatus configured to support examination as to whether the two fingerprint images indicate the fingerprints of the same finger and can reduce burden on a work of checking whether ridges are identical or not by the examiner.

Hereinafter, a specific exemplary embodiment will be described in further detail, with reference to the drawings. A same reference numeral is given to same components in the respective exemplary embodiments, and description of the same components will be omitted. A connection line between blocks in each drawing includes both of a bidirection and a monodirection. A one-way arrow schematically illustrates a main signal (data) stream and does not exclude bidirectionality.

First Exemplary Embodiment

A striped pattern image examination support apparatus according to a first exemplary embodiment will be described in detail with reference to the drawings.

Figure 2:
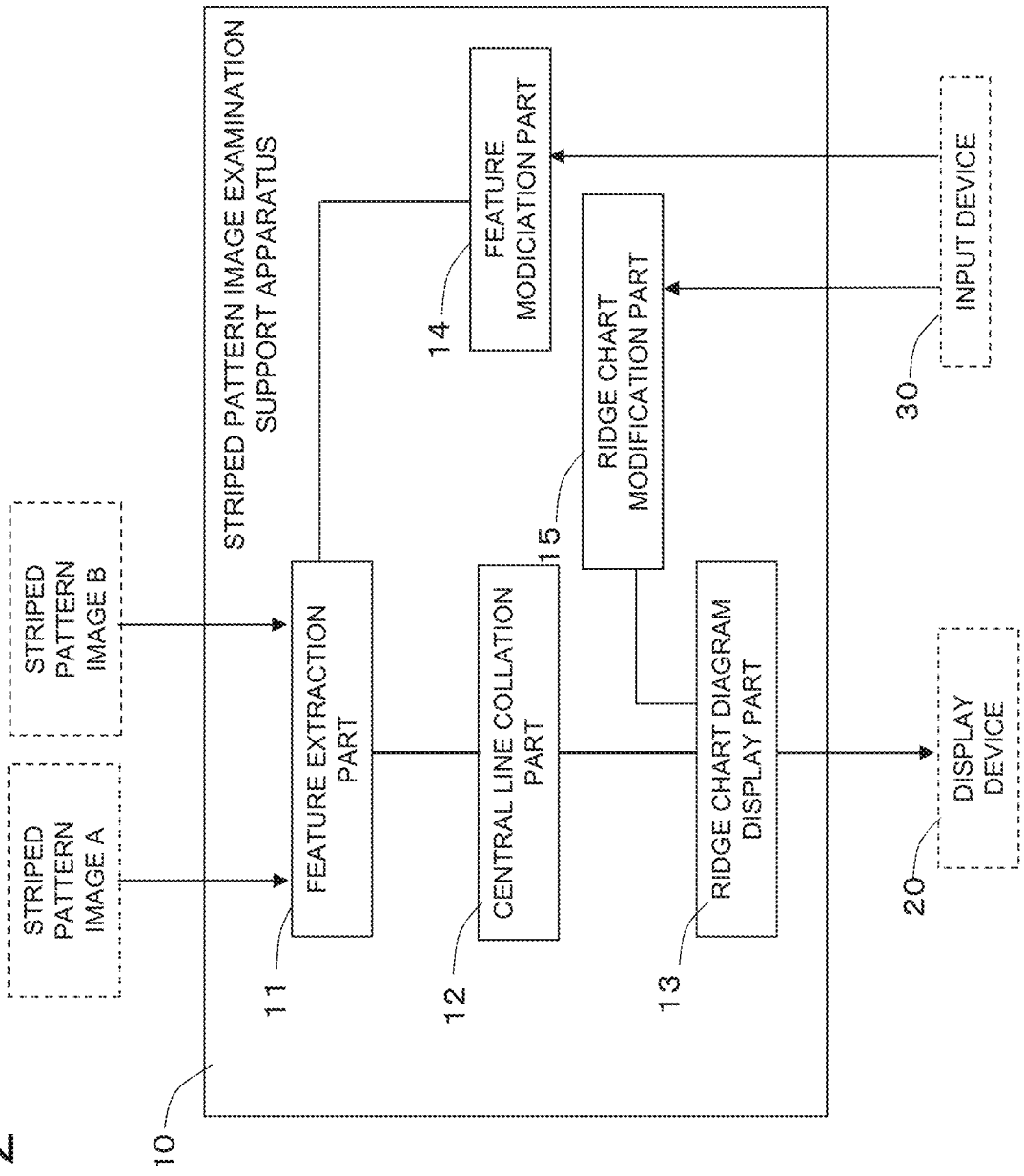
FIG. 2 is a diagram illustrating an example of a configuration of a striped pattern image examination support apparatus according to a first exemplary embodiment.

FIG. 2 is a diagram illustrating an example of a configuration of a striped pattern image examination support apparatus 10 according to the first exemplary embodiment. A display device 20 such as a display and an input device 30 such as a keyboard, a mouse, or a tablet are connected to the striped pattern image examination support apparatus 10.

A striped pattern image is an image including a curved stripe pattern formed by ridges. To take an example, a fingerprint image or a palmprint image including a region of a fingerprint or a palmprint is the striped pattern image. The striped pattern image may be, however, an image of a stripe including an ending point or a bifurcation point and is not limited to the fingerprint image or the palmprint image.

Corresponding ridges (ridge charts) refers to ridges, among ridges included in two striped pattern images, which have been determined to be the ridges extracted from locations of a same stripe pattern (or to be corresponding) between the two striped pattern images. Hereinafter, when it has been written just as a "ridge chart", the "ridge chart" indicates, out of corresponding ridges between the two striped pattern images, a ridge on one of the two striped pattern images. When it has been written as a "ridge chart pair", the "ridge chart pair" indicates a pair of a ridge on one image and a ridge on the other image corresponding to the ridge on the one image. When it has been written as a "plurality of ridge charts", the "plurality of ridge charts" indicate a plurality of ridges which are included in one image and to which a corresponding ridge is present in the other image. Usually, a central line is a skeletal line that is extracted from a ridge. In the disclosure of the present application, a ridge and a central line are treated to be the same unless otherwise specifically noted. That is, a ridge chart may indicate a corresponding central line (corresponding central line).

A central line and a feature point may be the ones automatically extracted from a striped pattern image by a computing machine or the like, using an existing arbitrary method, or may be the ones selected by a user or the like. Determination as to correspondence of central lines included in the two striped pattern images may be automatically made by the computing machine or the like, using an existing arbitrary method, or may be manually made by the user or the like.

[Hardware Configuration]

Subsequently, a hardware configuration of the striped pattern image examination support apparatus 10 according to the first exemplary embodiment will be described.

Figure 3:
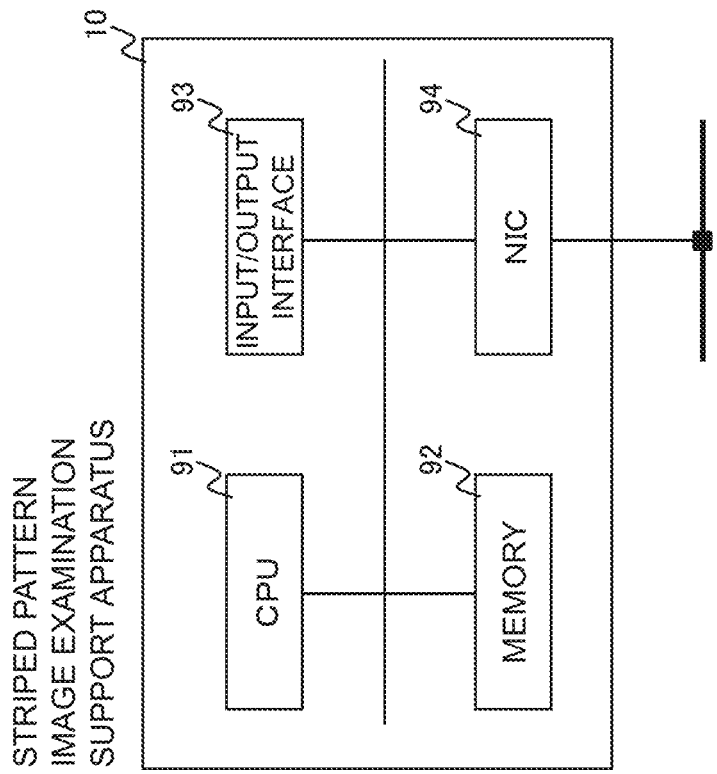
FIG. 3 is a block diagram illustrating an example of a hardware configuration of the striped pattern image examination support apparatus according to the first exemplary embodiment.

FIG. 3 is a block diagram illustrating an example of the hardware configuration of the striped pattern image examination support apparatus 10 according to the first exemplary embodiment.

The striped pattern image examination support apparatus 10 is implemented by a so-called information processing apparatus (computer), and includes the configuration illustrated in FIG. 3, for example. The striped pattern image examination support apparatus 10 includes a CPU (Central Processing Unit) 91, a memory 92, an input/output interface 93, and an NIC (Network Interface Card) 94 that is communication means, and so on, which are mutually connected by an internal bus.

The configuration illustrated in FIG. 3, however, does not intend to limit the hardware configuration of the striped pattern image examination support apparatus 10. The striped pattern image examination support apparatus 10 may include hardware not illustrated or may not include the NIC 94 or the like, as necessary. It does not also mean that the number of CPUs or the like that are included in the striped pattern image examination support apparatus 10 is not limited to the illustration in FIG. 3, and a plurality of the CPUs, for example, may be included in the striped pattern image examination support apparatus 10.

The memory 92 is a RAM (Random Access Memory), a ROM (Read Only Memory), or an auxiliary storage device (such as a hard disk).

The input/output interface 93 is means for serving as an interface for the display device 20 and the input device 30. The display device 20 is a liquid crystal display or the like, for example. The input device 30 is a device configured to accept a user operation using a keyboard or a mouse. An external storage device such as a USB (Universal Serial Bus) memory can be included in the input device 30.

Functions of the striped pattern image examination support apparatus 10 are implemented by various processing modules that will be described later. The processing modules are implemented by execution of a program stored in the memory 92 by the CPU 91. That program can be downloaded via a network or can be updated using a storage medium that has stored that program. The processing modules may be implemented by a semiconductor chip. That is, means for executing the functions of the processing modules using certain hardware and/or software may be provided.

Subsequently, processing configurations (of processing modules) of the striped pattern image examination support apparatus 10 according to the first exemplary embodiment will be described. Referring to FIG. 2, the striped pattern image examination support apparatus 10 is configured by including a feature extraction part 11, a central line collation part 12, a ridge chart diagram display part 13, a feature modification part 14, and a ridge chart modification part 15.

The feature extraction part 11 is means for extracting at least central lines and feature points from each of two striped pattern images, as a feature of each of the two striped pattern images. That is, the feature extraction part 11 is means for extracting from an image that is input to the striped pattern image examination support apparatus 10, a feature amount (such as the central lines and the feature points) that features the image. To take an example, the feature extraction part 11 extracts central lines and feature points from each of a striped pattern image A and a striped pattern image B, as illustrated in FIG. 2. The feature extraction part 11 also extracts ridge zones (zones) in the extraction process of the feature points.

Further, as will be described later, when the user manually modifies or inputs a feature point (such as in a case where the user has deleted or added the feature point), the feature extraction part 11 executes extraction of a central line holding the feature point that has been manually modified. Similarly, when the user manually modifies or inputs a central line or a zone, the feature extraction part 11 executes extraction of a feature point holding the central line or the zone. That is, the feature extraction part 11 is also means for extracting the central line again while holding the feature of a striped pattern image that has been modified by the user.

The central line collation part 12 is means for performing collation of the respective central lines of the two striped pattern images and computing corresponding central lines between the striped pattern images. That is, the central line collation part 12 performs collation of the central lines extracted from the two striped pattern images and outputs the corresponding central lines (corresponding central lines: ridge charts). The central line collation part 12 is also means for computing corresponding central lines again from the two striped pattern images using the central line extracted again by the feature extraction part 11.

The ridge chart diagram display part 13 is means for superimposing and displaying the central lines on each striped pattern image. When displaying the ridge charts, the ridge chart diagram display part 13 displays a ridge chart pair (the respective corresponding central lines of the two striped pattern images) using a same color and a same line type, thereby demonstrating a correspondence relationship in a ridge chart diagram. The ridge chart diagram display part 13 displays, side by side, (performs side-by-side display of) striped pattern images each with the ridge chart distinguished by the same color or the same line type superimposed thereon in order to demonstrate the correspondence between the two striped pattern images and the ridge charts. Such a diagram is referred to as the ridge chart diagram.

In addition to the display of the corresponding central line of each of the striped pattern images using the same color or the like as mentioned above, the ridge chart diagram display part 13 can take various measures when the ridge chart diagram display part 13 displays the ridge chart diagram. To take an example, the ridge chart diagram display part 13 can superimpose a certain one of a plurality of central lines computed from each striped pattern image on the striped pattern image by using a predetermined form (can perform a display for a corresponding central line) if the certain central line is the corresponding central line. If another one of the central lines is a noncorresponding central line, the ridge chart diagram display part 13 can superimpose the another central line on the striped pattern image by using a predetermined display for the noncorresponding central line. To take an example, the ridge chart diagram display part 13 may distinguish the corresponding central line and the noncorresponding central line that have been extracted from the striped pattern image by using different colors and may superimpose the corresponding central line and the noncorresponding central line on the striped pattern image. Further, on that occasion, the color or the line type of each of the corresponding central line and the noncorresponding central line to be superimposed on each striped pattern image may be made common between the two striped pattern images. Alternatively, the ridge chart diagram display part 13 may highlight and display the noncorresponding central line among the central lines extracted from the striped pattern images. The form (such as a change in the color of each central line or a change in the line type of the central line) by which the ridge chart diagram display part 13 superimposes and displays each central line on each striped pattern image may be set in advance, or may be determined by the user, using a menu or the like. The display form of each central line includes a form by which the central line is not displayed (not superimposed) on each striped pattern image. That is, only the noncorresponding line may be highlighted and displayed on each striped pattern image so that the user can immediately grasp the presence of the noncorresponding line.

As mentioned above, when displaying the ridge chart diagram, the ridge chart diagram display part 13 uses the corresponding central lines computed by the central line collation part 12. Specifically, the ridge chart diagram display part 13 refers to information on the above-mentioned computed corresponding central lines and determines whether or each of the plurality of central lines included in each striped pattern image is the "corresponding central line" or the "noncorresponding central line". Then, based on a determination result about each central line, the ridge chart diagram display part 13 determines the display form (such as the color or the line type of each central line) when the central line is superimposed on the striped pattern image, and displays the ridge chart diagram. That is, the ridge chart diagram display part 13 determines the display form of each central line based on whether or not the central line is the corresponding central line, and superimposes and displays the central line on the striped pattern image by the determined display form.

When the corresponding central lines are computed again by the central line collation part 12, the ridge chart diagram display part 13 determines the display form of each central line to be superimposed on each of the two striped pattern images, based on the corresponding central lines.

The ridge chart diagram display part 13 performs display of the ridge chart diagram on the display device 20 such as the display. The ridge chart diagram display part 13 may display a feature point chart diagram (refer to FIG. 9), as necessary.

The feature modification part 14 is means for performing feature modification of at least one of the two striped pattern images. Specifically, the feature modification part 14 independently performs feature modification such as a change in the type of a feature point, addition or deletion of a feature point, addition or deletion of a central line, addition or deletion of a zone, or the like for each of the two striped pattern images, by an operation by the user who has used the input device 30.

Further, the feature modification part 14 includes a function of automatically updating a feature point type in one of the striped pattern images to a feature point type in the other of the striped pattern images when the types of paired feature points respectively included in the two striped pattern images are mutually different. That is, when the feature point type such as an ending point or a bifurcation point is different between corresponding feature points between the two striped pattern images, the feature point modification part 14 can also update the feature point type of one of the two striped pattern images by the feature point type of the other of the two striped pattern images.

The ridge chart modification part 15 is means for changing the color type or the line type of the ridge chart and performing modification such as addition of a ridge chart or deletion of the ridge chart, by an operation by the user who has used the input device 30 that is a keyboard or a pointing device such as a mouse or a tablet. Since the ridge chart is associated between the two images, the ridge chart modification part 15 performs addition of the ridge chart and deletion of the ridge chart using both of the images. That is, the ridge chart modification part 15 is also means for accepting an operation by the user for changing the display form of the corresponding central line on the ridge chart diagram (of the two striped pattern images each with the central lines superimposed and displayed thereon) displayed by the ridge chart diagram display part 13.

Subsequently, the first exemplary embodiment will be described with reference to a flowchart illustrated in FIG. 4 and the drawings indicating examples of fingerprint images. On that occasion, a description will be given about a case where a ridge chart diagram of a remaining fingerprint illustrated in FIG. 5 and an impression fingerprint (impression fingerprint that becomes a pair of the remaining fingerprint in FIG. 5) illustrated in FIG. 6 is displayed by the striped pattern image examination support apparatus 10 according to the first exemplary embodiment.

Figure 4:
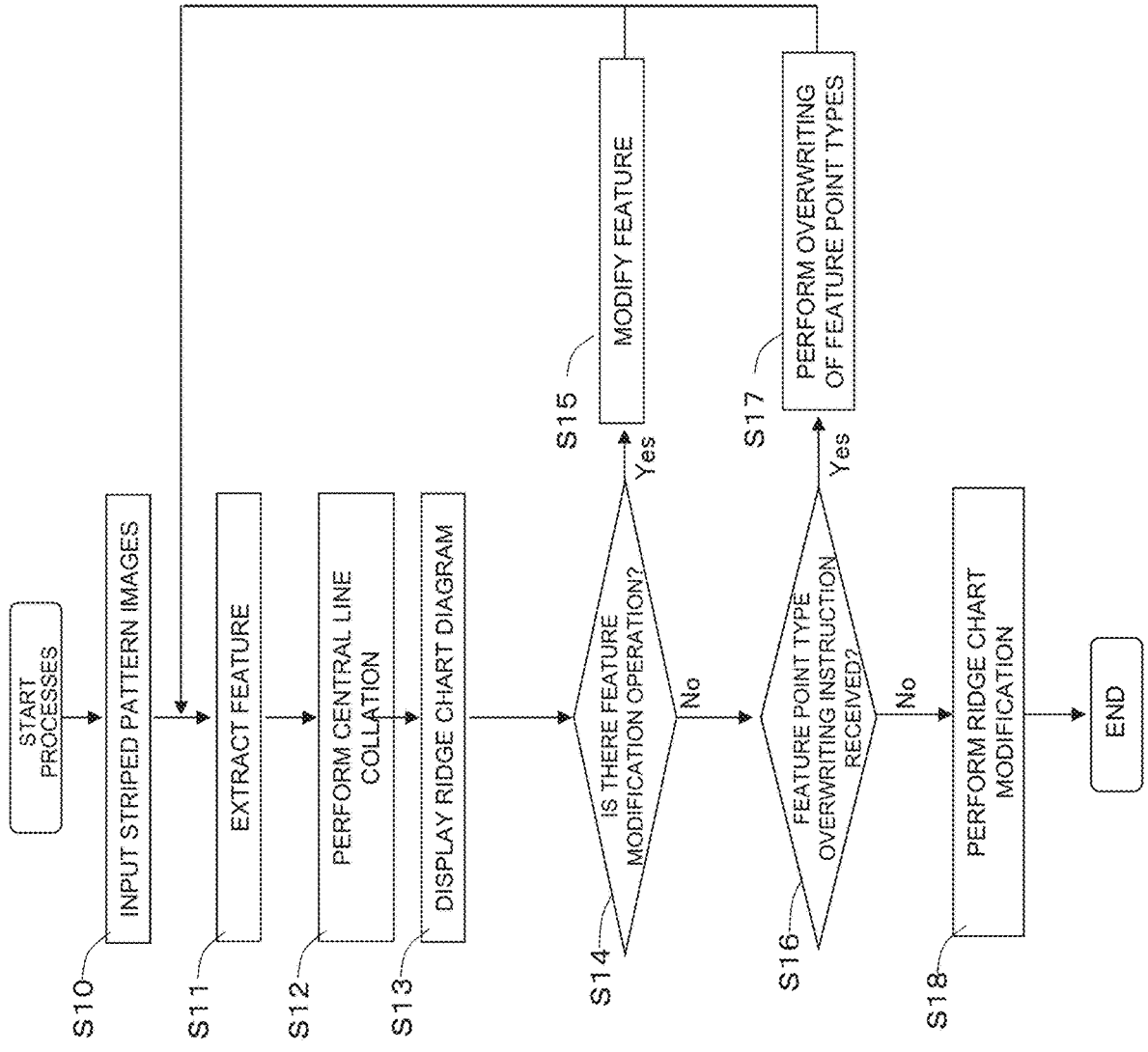
FIG. 4 is a flowchart illustrating an example of operations of the striped pattern image examination support apparatus according to the first exemplary embodiment.

Referring to FIG. 4, the feature extraction part 11 of the striped pattern image examination support apparatus 10 first receives two striped pattern images (step S10). The striped pattern images that are received by the striped pattern image examination support apparatus 10 may be obtained from an image input device such as a sensor or a scanner, or image data digitized and stored in advance may be obtained, using a USB memory or the like.

The remaining fingerprint is a fingerprint that has been left on a crime scene or the like, for example, and often has a poor quality. On contrast therewith, the impression fingerprint is a fingerprint taken for a registration purpose, and often has a good quality. Fingerprints for determination whether the fingerprints are identical or not may be remaining fingerprints or impression fingerprints. However, the determination whether the fingerprints are identical or not is often made between the remaining fingerprint and the impression fingerprint.

Figure 5:
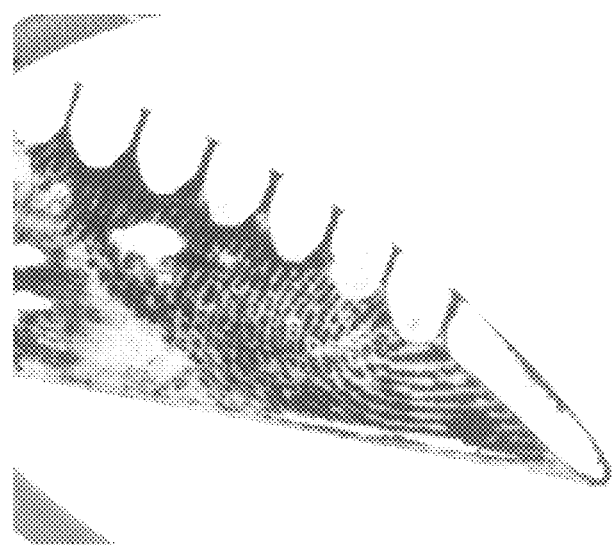
FIG. 5 is a diagram illustrating an example of a remaining fingerprint.
Figure 6:
FIG. 6 is a diagram illustrating an example of an impression fingerprint.

Examples of fingerprint images illustrated in FIGS. 5 and 6 and so on are obtained by digitizing fingerprint images read by a sensor or a scanner. The examples of the fingerprint images as mentioned above are obtained by the digitization with a resolution of 500 dpi, according to "ANSI/NIST-ITL-1-2000 Data Format for the Interchange of Fingerprint, Facial & Scar Mark & Tattoo (SMT) Information" that has been standardized at the NIST (National Institute of Standards and Technology) in the United States. The above-mentioned document on the standardization is disclosed in NIST Special Publication 500-245 in ANSI/NIST-ITL 1-2000 Revision of ANSI/NIST-CSL1-1993 & ANSI/NIST-ITL 1a-1997 (the URL for the document is <https://www.nist.gov/sites/default/files/documents/itl/ansi/sp500-245-a16.pdf)>.

Subsequently, the feature extraction part 11 extracts a feature (feature amount) of the fingerprint from each of the fingerprint images in FIGS. 5 and 6 (step S11). The feature of the fingerprint includes central lines and zones (ridge regions), in addition to feature points. Usually, feature point extraction is performed by thinning (central line formation of) each stripe included in a digitized striped pattern image and extracting an ending point and a bifurcation point from each central line obtained by thinning the stripe. The feature point extraction including the central line formation can be implemented, using a method described in Reference Literature 1 of "Handbook of Fingerprint Recognition p83-113, D. Maltoni, et. al., Springer".

Figure 7:
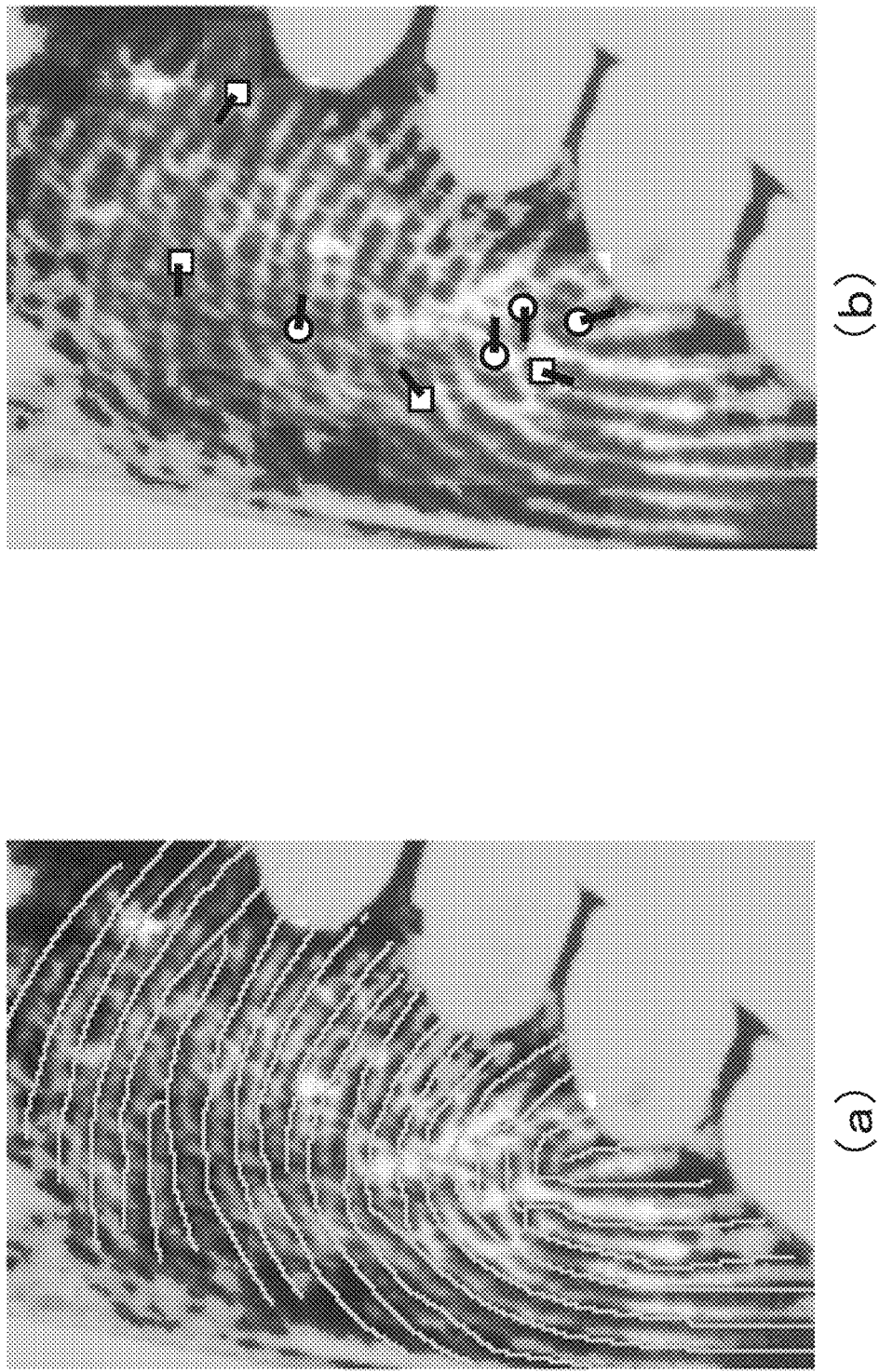

When the feature extraction process in step S11 is executed for the remaining fingerprint illustrated in FIG. 5, images illustrated in FIG. 7 are obtained. FIG. 7A illustrates an example where the extracted central lines are superimposed on the fingerprint image illustrated in FIG. 5. FIG. 7B illustrates an example where the extracted feature points and zones are superimposed on the fingerprint image in FIG. 5. With respect to the zones, regions that could not be recognized as ridges are displayed after having been filled in such a manner that the regions can be distinguished from the other regions. The feature points are extracted from the regions that could be recognized as the ridges. Further, an effective region for central line collation by the central line collation part 12 is a region where the ridge regions overlap with each other between two fingerprint images. In the following description, the effective region for the central line collation is written as a common effective region. Further, with respect to each feature point, an ending point is displayed as a circular mark, and a bifurcation point is written as a square mark in the drawings including FIG. 7.

Figure 8:
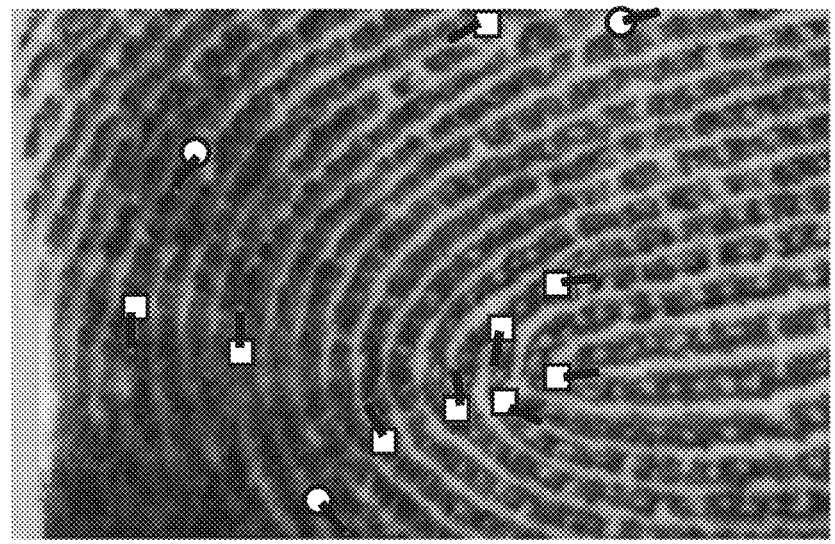
Figure 8:
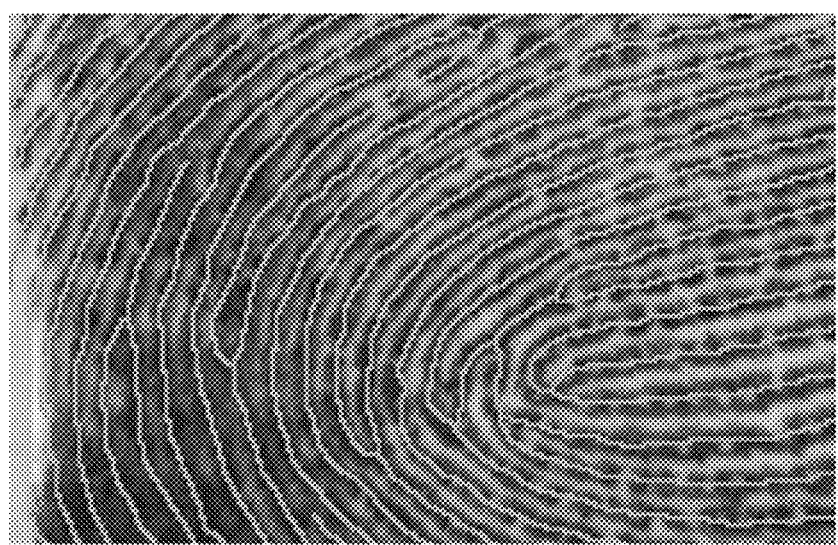

A similar process is performed for the impression fingerprint as well. Then, when the feature extraction process is executed for the fingerprint image in FIG. 6, images illustrated in FIG. 8 are obtained. FIG. 8A illustrates an example where the extracted central lines are superimposed on the fingerprint image in FIG. 6. FIG. 8B illustrates an example where the extracted feature points and zones are superimposed on the fingerprint image in FIG. 6. FIG. 8 describes the images obtained by cutting off a portion of the fingerprint image in FIG. 6.

Subsequently, the central line collation part 12 performs the central line collation (step S12). Specifically, the central line collation part 12 searches for a correspondence relationship with respect to each central line, using the central lines, the feature points, and the zones in the two striped pattern images that have been extracted by the feature extraction part 11. By searching for the correspondence relationship for each central line, the central line collation part 12 computes a ridge chart. The central line collation (ridge chart computation) can be implemented by a method disclosed in Reference Literature 2 (Japanese Patent No. 4030829), for example.

Figure 9:
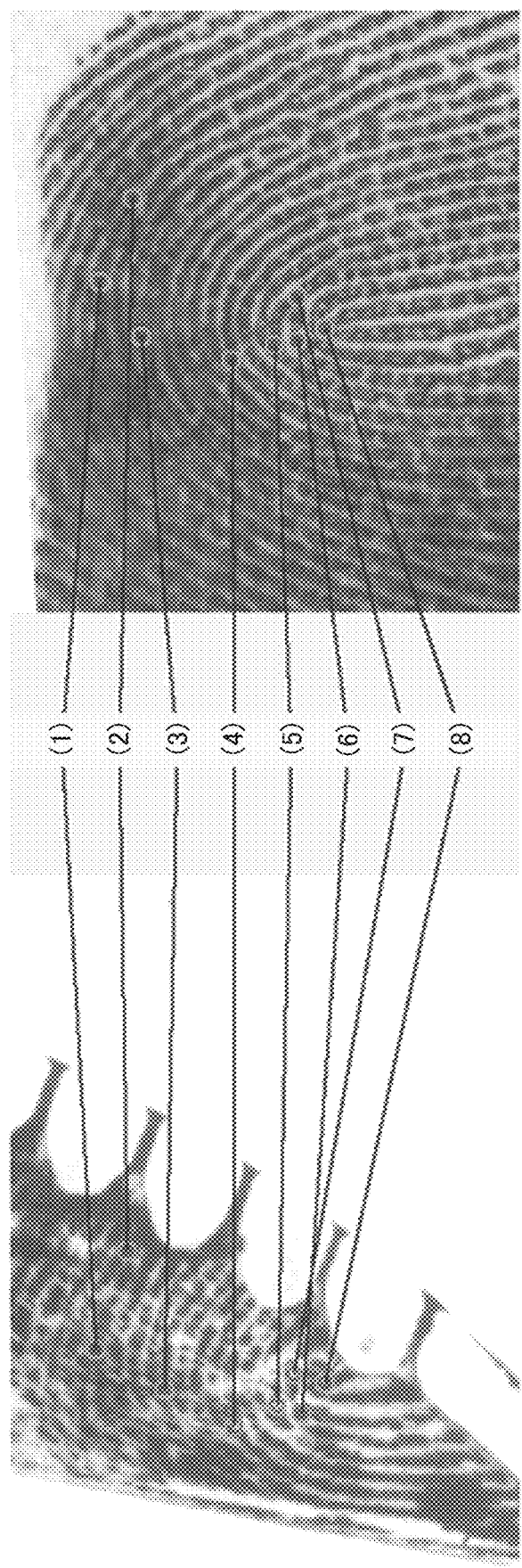
FIG. 9 is a diagram illustrating an example of a feature point chart diagram.

In the method disclosed in Reference Literature 2, feature point collation is first performed to determine whether or not the feature points match to each other. FIG. 9 is a feature point chart diagram using the feature point collation in accordance with the above-mentioned method and illustrates matching relationships (correspondence relationships) between the respective feature points. Usually, no distinction is made between feature point types (such as an ending point and a bifurcation point) in the feature point collation. Thus, even if the feature points have different feature point types between two fingerprints, the feature points are determined to correspond to each other. When FIG. 9 is checked, it can be found that eight feature points extracted from the remaining fingerprint have all correspondence relationships with the feature points in the impression fingerprint. In the method disclosed in Reference Literature 2, a correspondence relationship between central lines in the vicinity of feature points whose feature point types are different cannot be determined.

Figure 10:
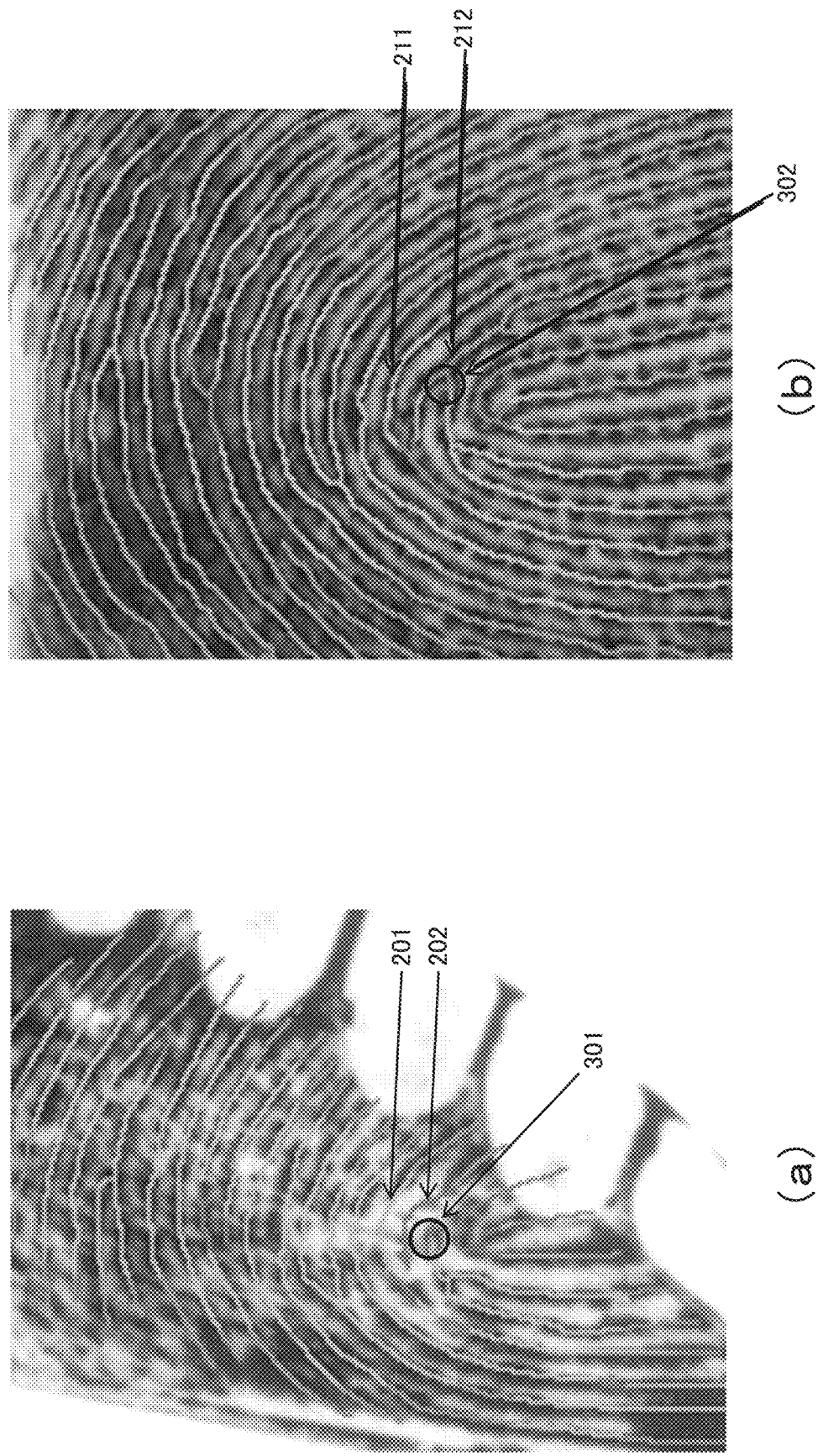
FIG. 10 includes FIG. 10A and FIG. 10B that constitute a diagram illustrating an example of a ridge chart diagram in which ridge charts are superimposed on each of FIG. 7A and FIG. 8A.

Subsequently, the ridge chart diagram display part 13 displays a ridge chart diagram by superimposing the ridge chart on each of the two striped pattern images (step S13). FIG. 10 includes FIGS. 10A and 10B that constitute a ridge chart diagram illustrating correspondence relationships between the central lines that have been subjected to the central line collation in the preceding step. FIG. 10A is a diagram obtained by superimposing the ridge chart on FIG. 7A, and FIG. 10B is a diagram obtained by superimposing the ridge chart on FIG. 8A. Referring to FIG. 10, the central lines (corresponding central lines) determined to correspond to each other are displayed in thin gray, and the central lines (noncorresponding central lines) determined not to correspond to each other in the common effective region are displayed in thick gray. Further, the central lines outside the common effective region are the central lines not for checking whether the central lines are identical or not. Thus, the central lines outside the common effective region are displayed in thinner gray so as not to be noticeable. To take an example, a central line 201 in FIG. 10A and a central line 211 in FIG. 10B are the (thin gray) central lines determined to correspond to each other. A central line 202 in FIG. 10A and a central line 212 in FIG. 10B are the (thick gray) central lines determined not to correspond to each other.

If the two fingerprint images are a correct pair, it is preferable that the central lines (noncorresponding central lines) that do not correspond to each other be not present in the common effective region. That is, if there are the noncorresponding central lines, it is necessary to eliminate the noncorresponding central lines by modifying the feature of the remaining fingerprint or the impression fingerprint. In other words, when there are the noncorresponding central lines even if the feature has been modified, it can be said that two fingerprints should not be determined to be identical.

When FIG. 10 is checked, it can be seen that feature point types in the vicinity of the noncorresponding central lines displayed in thick gray are different between the remaining fingerprint and the impression fingerprint. To take an example, the feature point positioned in a region 301 in the vicinity of the central line 202 is an ending point. On contrast therewith, the feature point positioned in a region 302 in the vicinity of the central line 212 is a bifurcation point.

Further, when FIG. 7B and FIG. 8B are compared, it can be seen that, among eight paired feature points in the remaining fingerprint (on the left side of FIG. 9) illustrated in FIG. 9, the types of five paired feature points pertaining to (2), (3), (5), (7), and (8) are different from the feature point types in the impression fingerprint.

When a user who has seen the charting screen illustrated in FIG. 9 and the ridge chart diagram illustrated in FIG. 10 determines that the feature with respect to one of the feature points, the central lines, and the zones that have been automatically extracted by the apparatus is not appropriate, he tries to modify the feature. In that case, the feature modification part 14 accepts a feature modification operation by the user. Specifically, if the feature modification part 14 has accepted the feature modification operation by the user (Yes branching in step S14), the feature modification part 14 modifies one of the feature points or the like of the finger print image according to the operation (step S15). The modification of the feature includes a feature point modification, a central line modification, or a zone modification.

Figure 11:
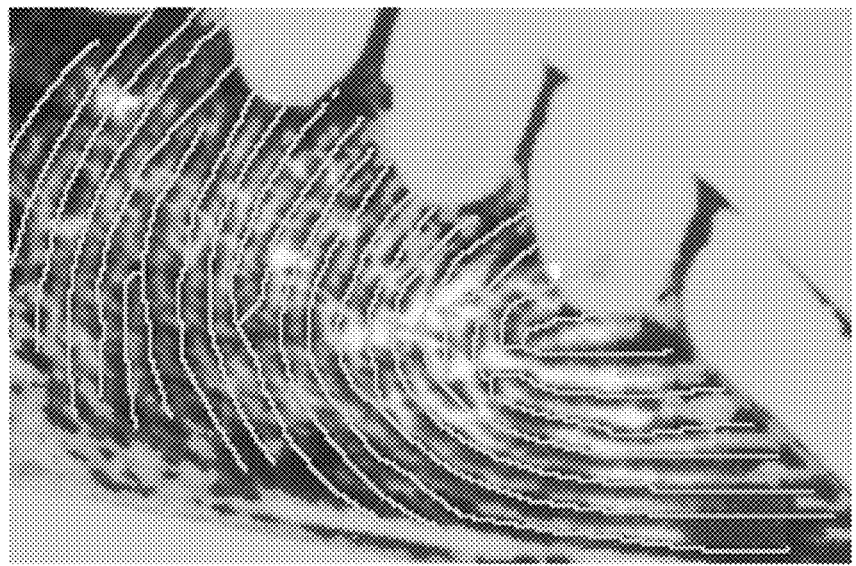
Figure 11:
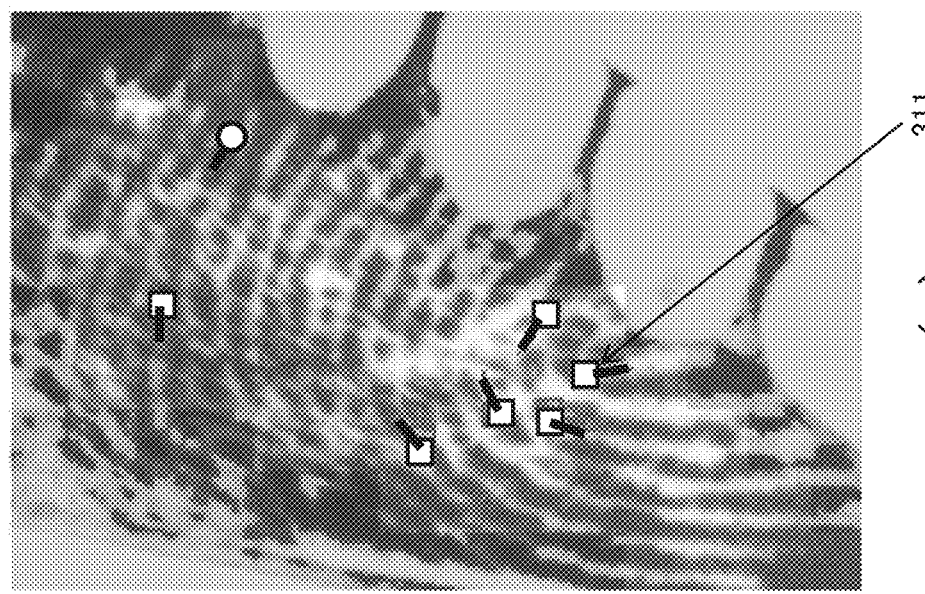

FIG. 11A is a diagram illustrating an example where, with respect to the five feature points illustrated in FIG. 9 and having the different feature point types, the feature point types in the remaining fingerprint have been manually modified by the user. To take an example, though the feature point type of a feature point 311 in FIG. 11A before the modification is an ending point (refer to FIG. 7B), the type of the feature point is modified to a bifurcation point by the modification by the user. With such a modification operation, the feature point types in the remaining fingerprint are made to match those in the impression fingerprint.

In the description about steps S14 and S15, the description has been given about the example where five feature point types in the remaining fingerprint are individually modified manually. Usually, an impression fingerprint has a better quality than a remaining fingerprint. Thus, the impression fingerprint often has correct feature point types. Accordingly, by overwriting the feature point types in the impression fingerprint on those in the remaining fingerprint, the feature point types in the two fingerprints can also be matched, without individual modifications of the feature point types in the remaining fingerprint by the user.

Specifically, the feature modification part 14 may overwrite the feature point types in the impression fingerprint on the feature point types in the remaining fingerprint with respect to the corresponding feature points whose feature point types are different, using acceptance of a special operation (such as a feature point type overwriting instruction operation using a menu screen or the like) by the user, as a trigger (the feature point types in the remaining fingerprint may be matched to the feature point types in the impression fingerprint). More specifically, the feature modification part 14 determines whether or not a "feature point type overwriting instruction" has been input from the user, and the feature point types in the remaining fingerprint are overwritten by the feature point types in the impression fingerprint (step S17) if the instruction is input (Yes branching in step S16).

It is also a rational response to change, by approximately five pixels (a half of 10 pixels that are equivalent to a mean ridge interval) at a maximum, positions of the feature points in the remaining fingerprint for which the overwriting has been performed, in consideration of displacement of positions of the feature points in the impression fingerprint after coordinate transformation. The positions of the feature points in the impression fingerprint after the coordinate conversion can be computed by an existing triangular transformation technology such as a Helmert (Helmert) transformation, using coordinates of the paired feature points extracted by the feature point collation.

If the feature has been modified in step S15, feature extraction of holding modified feature data (manual feature) is performed (step S11). When one of the feature points has been manually modified, the feature extraction that holds the manual feature point can be implemented by a method disclosed in Reference Literature 3 (JP Patent Kokai Publication No. JP-P-2016-045501A), for example. In the method disclosed in Reference Literature 3, a central line that matches the manual feature point is generated. FIG. 11B is a diagram illustrating each central line generated as mentioned above. If one of the central lines has been manually modified, the feature point should be just extracted from the central line.

Subsequently, the central line collation part 12 searches for a correspondence relationship with respect to each central line, using the central lines, the feature points, and the zones of the two striped pattern images extracted by using the feature that has been manually modified (step S12). Since description of the central line collation has already given, the description will be omitted.

Subsequently, the ridge chart diagram display part 13 superimposes and displays a ridge chart on each of the two striped pattern images (step S13).

Figure 12:
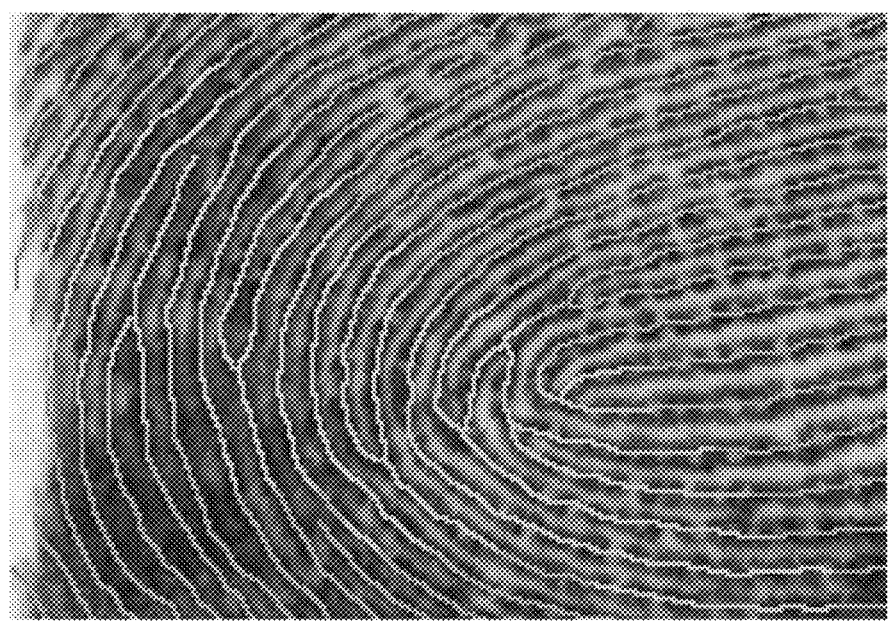
FIG. 12 includes FIG. 12A and FIG. 12B that are diagrams each illustrating correspondence relationships between central lines after the feature point modification.
Figure 12:
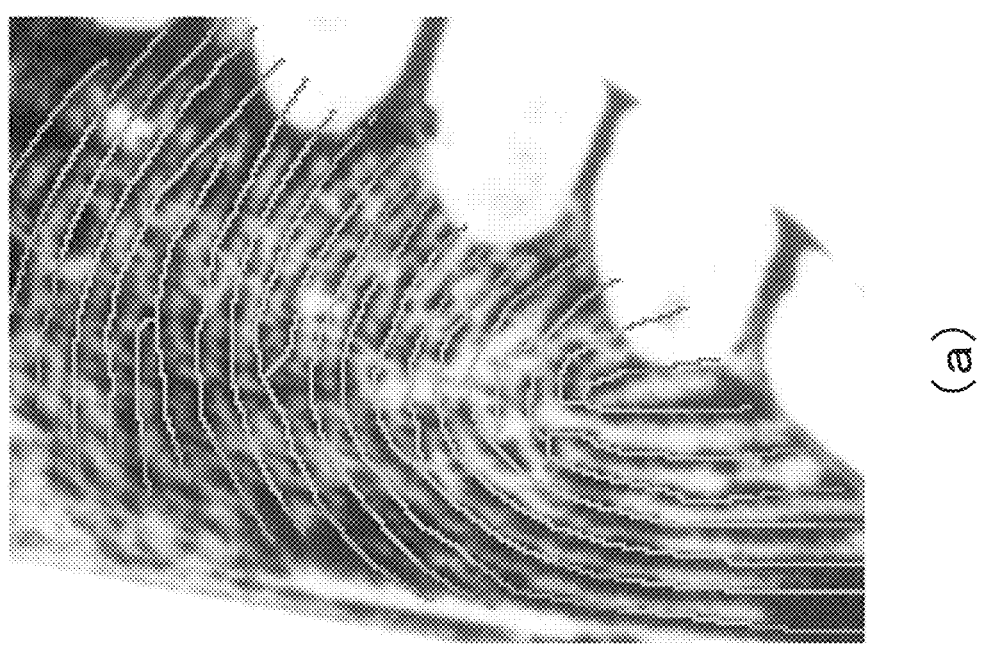

FIG. 12 includes FIG. 12A and FIG. 12B that are diagrams each illustrating correspondence relationships between the central lines after the feature modification. FIG. 12A is a diagram that is the same as the diagram illustrated in FIG. 11B, and FIG. 12B is a diagram that is the same as the diagram illustrated in FIG. 8A. When FIG. 12 is checked, it can be seen that the correspondence relationships of all ridges within the common effective region have been established between the two fingerprints without contradiction because no noncorresponding central line displayed in the thick gray is present in either of the drawings.

Figure 13:
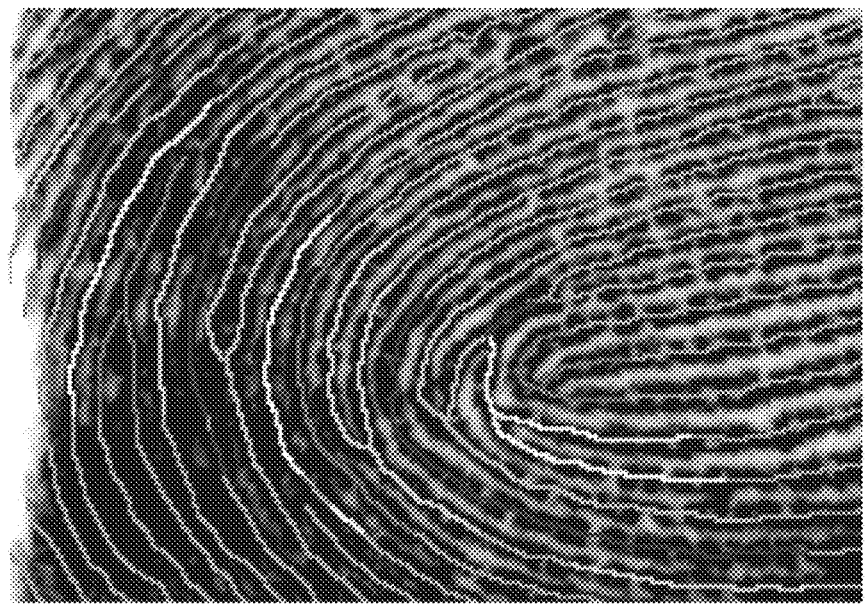
FIG. 13 includes FIG. 13A and FIG. 13B for explaining an operation of a ridge chart modification part.
Figure 13:
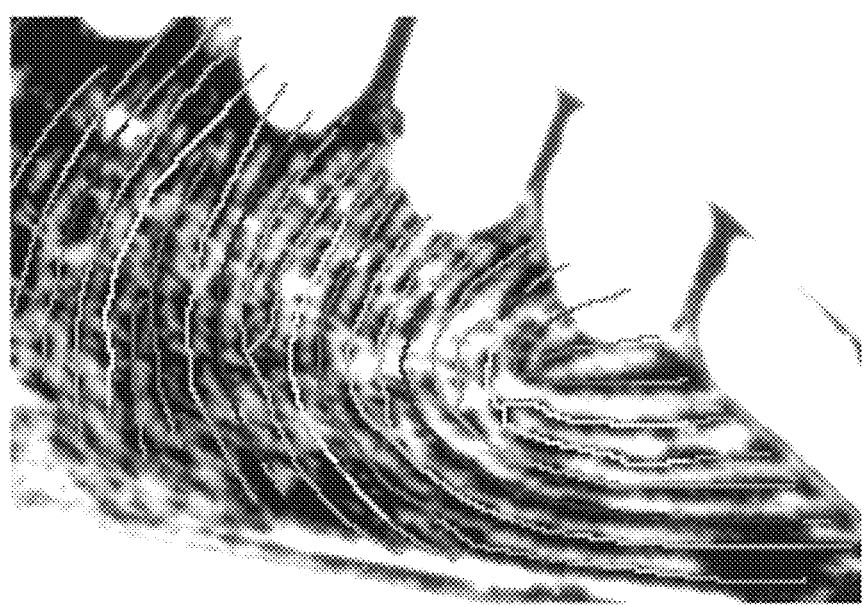

The user may modify a color type or a line type in order to distinguish each ridge chart. Specifically, the ridge chart modification part 15 accepts a ridge chart modification operation by the user (step S18). To take an example, the user distinguishes the individual ridge charts in the ridge chart diagram in FIG. 12 by using different colors, as illustrated in FIG. 13. When FIG. 13 is checked, it can be seen that the correspondence relationships between the ridges in the two fingerprints can be readily understood even by a non-expert of the fingerprint. FIG. 13 demonstrates the correspondence relationships between the ridges by using light and dark (graduations) of the ridge charts.

As described above, the striped pattern image examination support apparatus 10 according to the first exemplary embodiment extracts the central lines and the feature pints from each of the two striped pattern images and computes the corresponding central lines (ridge charts) between the images. Then, when information pertaining to the corresponding central lines is reflected on the two striped pattern images, the striped pattern image examination support apparatus 10 takes a measure such as distinguishing the corresponding lines and the noncorresponding lines by using the different colors, thereby allowing immediate determination as to whether or not the two striped pattern images are from a same object to be made by the user. That is, if one of the noncorresponding lines is present in a region targeted for the central line collation, it is determined that the two images are not from the same object. Alternatively, even if one of the noncorresponding central lines is present in the region targeted for the central line collation, the striped pattern image examination support apparatus 10 can present, to the user, information for making a decision as to whether the presence of the noncorresponding central line is caused by a difference in the feature point type or the like. When the noncorresponding central line is changed to a corresponding central line and no noncorresponding central line is present by a modification in a rational range such as a feature point type change in this case, it is determined that the two striped pattern images are from the same object.

The configuration of the striped pattern image examination support apparatus 10 (in FIG. 2) described in the above-mentioned exemplary embodiment is an illustration and does not intend to limit the configuration of the apparatus. It may be so configured, for example, that the ridge chart diagram display part 13 does not display the feature point chart diagram, and another display part is provided and the another display part displays the feature point chart diagram.

Alternatively, it may be so configured that means (determination part) for determining whether or not one of the noncorresponding central lines is present within the common effective region is provided, and if it is determined by the means that no corresponding central line is present, presence of no corresponding central line is notified to the user. That is, it may be so configured that the striped pattern image examination support apparatus 10 explicitly displays that there is no corresponding central line on the two striped pattern images. In this case, the need for the user to check the ridge chart diagram and determine whether the two striped pattern images are from the same object is eliminated.

In the above-mentioned exemplary embodiment, the description has been given about a case where the feature modification that is manually performed by the user (in steps S14 and S15 in FIG. 4) and the automatic feature modification (in steps S16 and S17) by the apparatus coexist. It may be so configured, however, that the striped pattern image examination support apparatus 10 accommodates one of the feature modifications. Alternatively, two feature modifications may be controlled to cooperate with each other. To take an example, when a noncorresponding central line is present in the central line collation process after the feature modification that has been manually performed, the striped pattern image examination support apparatus 10 may perform the automatic feature modification by the apparatus. In this case, a noncorresponding central line that cannot be accommodated by visual feature modification (feature modification that is manually performed) by the user can be set not to be present.

By installing the above-mentioned computer program in the storage part of the computer, the computer can be functioned as the striped pattern image examination support apparatus. Further, by causing the computer to execute the above-mentioned computer program, the striped pattern image examination support method can be executed by the computer.

A plurality of steps (processes) are sequentially described in a plurality of flowcharts used in the above-mentioned description. However, the execution order of the steps to be executed in each exemplary embodiment is not limited to the order in that description. In each exemplary embodiment, the order of the steps that are illustrated can be subjected to a change in a range which does not cause a trouble to the contents, such as execution of the respective steps in parallel. Alternatively, the contents described in the above-mentioned respective exemplary embodiments can be combined in a range without inconsistency.

Part or all of the above-mentioned exemplary embodiment can be described as the followings but is not limited to the followings.

[First Mode]

See the striped pattern image examination support apparatus according to the first aspect.

[Second Mode]

The striped pattern image examination support apparatus, preferably according to the first mode, further comprising:

a feature modification part to modify the feature of at least one of the first and second striped pattern images, wherein the feature extraction part extracts a central line again while holding the feature of the at least one of the striped pattern images that has been modified by the feature modification part;

the central line collation part computes corresponding central lines from the first and second striped pattern images, using the central line that has been extracted again; and the display part determines a display form of each of the central lines based on the corresponding central lines that have been computed again.

[Third Mode]

The striped pattern image examination support apparatus, preferably according to the second mode, wherein when types of paired feature points respectively included in the first and second striped pattern images are mutually different, the feature modification part overwrites a feature point type of one of the striped pattern images on a feature point type of the other of the striped pattern images.

[Fourth Mode]

The striped pattern image examination support apparatus, preferably according to any one of the first to third modes, further comprising:

a modification part to accept an operation for changing, by a user, the display form of the corresponding central lines in the first and second striped pattern images with the central lines superimposed and displayed thereon, wherein the display part superimposes and displays the central lines on each of the first and second striped pattern images according to a display form that has been changed by the user.

[Fifth Mode]

The striped pattern image examination support apparatus, preferably according to any one of the first to fourth modes, wherein the feature extraction part extracts, from each of the first and second striped pattern images, ridge regions including ridges and non-ridge regions not including the ridges; and the central line collation part sets a region where the ridge regions in the respective first and second striped pattern images overlap with each other to a target for the central line collation.

[Sixth Mode]

The striped pattern image examination support apparatus, preferably according to any one of the first to fifth modes, wherein the display part changes the display form of the corresponding central lines and the display form of a noncorresponding central line(s) other than the corresponding central lines and superimposes and displays the corresponding central lines and the noncorresponding central line(s) on each of the first and second striped pattern images.

[Seventh Mode]

The striped pattern image examination support apparatus, preferably according to the third mode, wherein the feature modification part performs overwriting of the feature point type when a predetermined operation is input.

[Eighth Mode]

The striped pattern image examination support apparatus, preferably according to the seventh mode, wherein the feature modification part overwrites the feature point type of an impression fingerprint image on the feature point type of a remaining fingerprint image.

[Ninth Mode]

See the striped pattern image examination support method according to the second aspect.

[Tenth Mode]

See the program according to the third aspect.

The ninth and tenth modes can be developed into the second to eighth modes.

The disclosure of the above-mentioned Patent Literatures and so on that have been cited is incorporated herein in its entirety by reference. Modification and adjustment of each exemplary embodiment or each example are possible within the scope of the overall disclosure (including the claims) of the present invention and based on the basic technical concept of the present invention. Various combinations or selections of various disclosed elements (including each element in each claim, each element in each exemplary embodiment or each example, and each element in each drawing) are possible within the scope of the overall disclosure of the present invention. That is, the present invention naturally includes various variations and modifications that could be made by those skilled in the art according to the overall disclosure including the claims and the technical concept. With respect to a numerical value range described herein in particular, an arbitrary numerical value and a small range included in the numerical value range should be construed to be specifically described even unless otherwise explicitly described.

REFERENCE SIGNS LIST 10, 100 striped pattern image examination support apparatus
11, 101 feature extraction part
12, 102 central line collation part
13 ridge chart diagram display part
14 feature modification part
15 ridge chart modification part
20 display device
30 input device
91 CPU (Central Processing Unit)
92 memory
93 input/output interface
94 NIC (Network Interface Card)
103 display part
201, 202, 211, 212 central line
301, 302 region
311 feature point

What is claimed is:

1. A striped pattern image examination support apparatus comprising:

at least one memory storing instructions: and at least one processor configured to execute the instructions to:

extract at least central lines and feature points from each of first and second striped pattern images, as a feature of each of the first and second striped pattern images;

collate the respective central lines of the first striped pattern image and the second striped pattern image and compute corresponding central lines between the first and second striped pattern images;

determine a display form of each of the central lines based on the computed corresponding central lines and superimpose and display the central lines on each of the first and second striped pattern images, according to the determined display form;

modify the feature of at least one of the first and second striped pattern images;

extract the central lines again while holding the feature of the at least one of the striped pattern images that has been modified by the feature;

compute corresponding central lines from the first and second striped pattern images, using the central line that has been extracted again; and determine a display form of each of the central lines based on the corresponding central lines that have been computed again.

2. The striped pattern image examination support apparatus according to claim 1, wherein when types of paired feature points respectively included in the first and second striped pattern images are mutually different, the instructions include to overwrite a feature point type of one of the striped pattern images on a feature point type of the other of the striped pattern images.

3. The striped pattern image examination support apparatus according to claim 1, the instructions further comprising:

to accept an operation for changing, by a user, the display form of the corresponding central lines in the first and second striped pattern images with the central lines superimposed and displayed thereon; and to superimpose and display the central lines on each of the first and second striped pattern images according to a display form that has been changed by the user.

4. The striped pattern image examination support apparatus according to claim 1, the instructions further comprising:

to extract, from each of the first and second striped pattern images, ridge regions including ridges and non-ridge regions not including the ridges; and to set a region where the ridge regions in the respective first and second striped pattern images overlap with each other to a target for the central line collation.

5. The striped pattern image examination support apparatus according to claim 1, the instructions further comprising:

to change the display form of the corresponding central lines and the display form of a noncorresponding central line(s) other than the corresponding central lines and to superimpose and display the corresponding central lines and the noncorresponding central line(s) on each of the first and second striped pattern images.

6. The striped pattern image examination support apparatus according to claim 2, the instructions further comprising:

to overwrite the feature point type when a predetermined operation is input.

7. The striped pattern image examination support apparatus according to claim 6, the instructions further comprising:

to overwrite the feature point type of an impression fingerprint image on the feature point type of a remaining fingerprint image.

8. A striped pattern image examination support method comprising:

extracting at least central lines and feature points from each of first and second striped pattern images, as a feature of each of the first and second striped pattern images;

performing collation of the respective central lines of the first striped pattern image and the second striped pattern image and computing corresponding central lines between the first and second striped pattern images;

determining a display form of each of the central lines based on the computed corresponding central lines and superimposing and displaying the central lines on each of the first and second striped pattern images, according to the determined display form;

modifying the feature of at least one of the first and second striped pattern images;

extracting the central lines again while holding the feature of the at least one of the striped pattern images that has been modified by the feature;

computing corresponding central lines from the first and second striped pattern images, using the central line that has been extracted again; and determining a display form of each of the central lines based on the corresponding central lines that have been computed again.

9. A non-transitory computer-readable recording medium storing thereon a program configured to cause a computer to execute:

a process of extracting at least central lines and feature points from each of first and second striped pattern images, as a feature of each of the first and second striped pattern images;

a process of performing collation of the respective central lines of the first striped pattern image and the second striped pattern image and computing corresponding central lines between the first and second striped pattern images;

a process of determining a display form of each of the central lines based on the computed corresponding central lines and superimposing and displaying the central lines on each of the first and second striped pattern images, according to the determined display form;

a process of modifying the feature of at least one of the first and second striped pattern images;

a process of extracting the central lines again while holding the feature of the at least one of the striped pattern images that has been modified by the feature;

a process of computing corresponding central lines from the first and second striped pattern images, using the central line that has been extracted again; and a process of determining a display form of each of the central lines based on the corresponding central lines that have been computed again.

* * * * *